United States Patent
Haupt et al.

(10) Patent No.: US 10,456,044 B2
(45) Date of Patent: Oct. 29, 2019

(54) SYSTEMS AND METHODS FOR GENERATING NON-CONTACT ULTRASOUND IMAGES USING PHOTOACOUSTIC ENERGY

(71) Applicant: Massachusetts Institute of Technology, Cambridge, MA (US)

(72) Inventors: Robert W. Haupt, Lexington, MA (US); Charles M. Wynn, Groton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1134 days.

(21) Appl. No.: 14/538,698

(22) Filed: Nov. 11, 2014

(65) Prior Publication Data
US 2015/0148655 A1   May 28, 2015

Related U.S. Application Data

(60) Provisional application No. 61/907,843, filed on Nov. 22, 2013.

(51) Int. Cl.
*A61B 5/00* (2006.01)
*G01N 21/17* (2006.01)
(Continued)

(52) U.S. Cl.
CPC .......... *A61B 5/0095* (2013.01); *A61B 8/0808* (2013.01); *A61B 8/0875* (2013.01);
(Continued)

(58) Field of Classification Search
None
See application file for complete search history.

(56) References Cited

U.S. PATENT DOCUMENTS 5,615,675 A   4/1997   O'Donnell et al.
5,840,023 A   11/1998  Oraevsky et al.
(Continued)

FOREIGN PATENT DOCUMENTS

DE   102008049692 A1   4/2010
EP      0996469 B1      8/2003
(Continued)

OTHER PUBLICATIONS

Karppinen et al. "Phase-delayed laser diode array allows ultrasonic guided wave mode selection and tuning", Journal of Applied Physics, (Apr. 14, 2013 American Institute of Physics, US) vol. 113, nr. 14, pp. 144904-144904-5.*

(Continued)

*Primary Examiner* — Joel F Brutus
(74) *Attorney, Agent, or Firm* — Quarles & Brady LLP

(57) ABSTRACT

A system and method for generating ultrasound images of a subject without physically contacting the subject is provided. A photoacoustic excitation source may be employed that directed into a scanning mirror to transmit acoustic disturbances into a patient to induce propagating photoacoustic waves. The acoustic disturbances are translated along the patient in a defined direction to cause coherent summation of the propagating photoacoustic waves and, thereby, a resultant acoustic and/or elastic wave to probe structures within the patient. Vibrations created by the backscatter of the resultant wave are detected at the surface of the patient and ultrasound images of the structures within the patient are generated. Detection of the vibrations may be performed using a laser vibrometer. The excitation and detection systems may be used separately or in combination.

50 Claims, 13 Drawing Sheets

(51) Int. Cl.
*A61B 8/08* (2006.01)
*A61B 8/10* (2006.01)
(52) U.S. Cl.
CPC ........... *A61B 8/10* (2013.01); *G01N 21/1702* (2013.01); *A61B 5/0064* (2013.01); *A61B 2560/0431* (2013.01); *A61B 2562/0204* (2013.01)

(56) References Cited

U.S. PATENT DOCUMENTS

| | | | |
|---|---|---|---|
| 6,292,682 | B1 | 9/2001 | Kruger |
| 8,203,911 | B2 | 6/2012 | Kremeyer |
| 8,260,403 | B2 | 9/2012 | Fukutani et al. |
| 2010/0010346 | A1 | 1/2010 | Greenleaf et al. |
| 2010/0245766 | A1 | 9/2010 | Zhang et al. |
| 2011/0048135 | A1* | 3/2011 | Caron ............... G01N 29/2418 73/633 |
| 2012/0326055 | A1 | 12/2012 | Wilson et al. |
| 2012/0330157 | A1 | 12/2012 | Mandella et al. |
| 2013/0023752 | A1* | 1/2013 | Khuri-Yakub ....... A61B 5/0095 600/407 |
| 2013/0041247 | A1 | 2/2013 | Maswadi |
| 2014/0196544 | A1* | 7/2014 | Wanda ............... A61B 5/14542 73/655 |
| 2014/0243666 | A1* | 8/2014 | Moilanen ............ A61B 8/0875 600/437 |
| 2015/0335252 | A1* | 11/2015 | Hirota ................. A61B 5/0095 600/407 |
| 2016/0066786 | A1* | 3/2016 | Kontiola ............... A61B 3/165 600/398 |

FOREIGN PATENT DOCUMENTS

| | | | | |
|---|---|---|---|---|
| WO | | 2009103502 | A1 | 8/2009 |
| WO | | 2013064740 | A1 | 5/2013 |
| WO | WO | 2013064740 | A1 * | 5/2013 ........... A61B 8/0875 |

OTHER PUBLICATIONS

Allen, et al., Generating Photoacoustic Signals Using High-Peak Power Pulsed Laser Diodes, Proc. SPIE, 2005, 5696:233-242.

Haupt, et al., Standoff Acoustic Laser Technique to Locate Buried Land Mines, Lincoln Laboratory Journal, 2005, 15(1):3-22.

Jiang, et al., Laser Vibrometry from a Moving Ground Vehicle, Applied Optics, 2011, 50(15):2263-2273.

Karppinen, et al., Phase-Delayed Laser Diode Array Allows Ultrasonic Guided Wave Mode Selection and Tuning, Journal of Applied Physics, 2013, 113:144904-1 thru 144904-5.

Li, et al., Photoacoustic Tomography and Sensing in Biomedicine, Phys. Med. Biol., 2009, 54(19):R59-R97.

Maslov, et al., Photoacoustic Imaging of Biological Tissue with Intensity-Modulated Continuous-Wave Laser, Journal of Biomedical Optics, 2008, 13(2):024006-1 thru 024006-5.

Moilanen, et al., Photo-Acoustic Phase-Delayed Excitation of Guided Waves in Coated Bone Phantoms, 2013 IEEE International Ultrasonics Symposium, 2013, pp. 2080-2083.

Ripoll, et al., Quantitative Point Source Photoacoustic Inversion Formulas for Scattering and Absorbing Media, Phys. Rev. E, 2005, 71:031912 [Abstract Only].

Rousseau, et al., Non-Contact Photoacoustic Tomography and Ultrasonography for Tissue Imaging, Biomedical Optics Express, 2012, 3(1):16-25.

Schurig, et al., Signal Analysis of Transients in Pulsed Photoacoustic Spectroscopy, Review of Scientific Instruments, 1993, 64(2):363-373.

Wang, Tutorial on Photoacoustic Microscopy and Computed Tomography, IEEE Journal of Selected Topics in Quantum Electronics, 2008, 14(1)171-179.

Wynn, et al., Dynamic Photoacoustic Spectroscopy for Trace Gas Detection, Applied Physics Letters, 2012, 101:184103-1 thru 184103-4.

Xu, et al., Photoacoustic Imaging in Biomedicine, Review of Scientific Instruments, 2006, 77:041101-1 thru 041101-22.

Xu, et al., Non-Contact Photoacoustic Tomography with a Laser Doppler Vibrometer, Proc. of SPIE, 2014, 8943:894332-1 thru 894332-7.

Yin, et al., Fast Photoacoustic Imaging System Based on 320-Element Linear Transducer Array, Phys. Med. Biol., 2004, 49:1339-1346.

PCT International Search Report and Written Opinion, PCT/US2014/065001, dated Feb. 5, 2015.

* cited by examiner

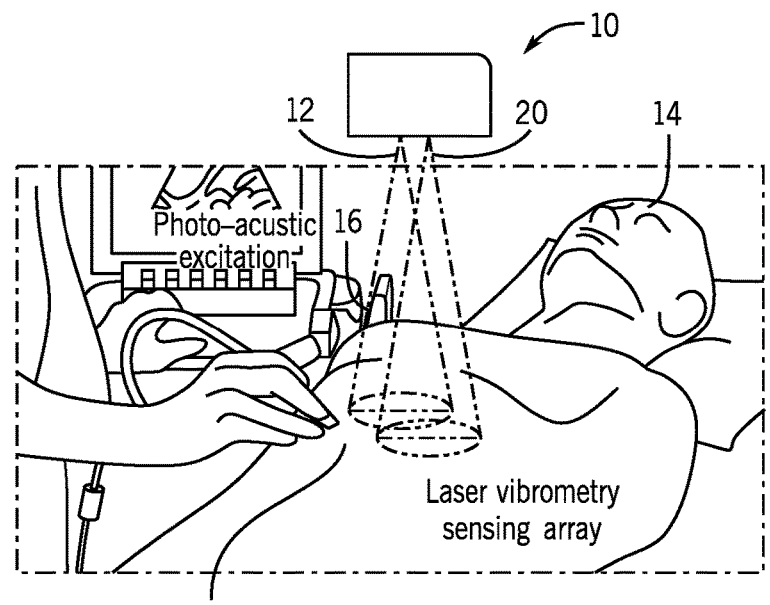
FIG. 2
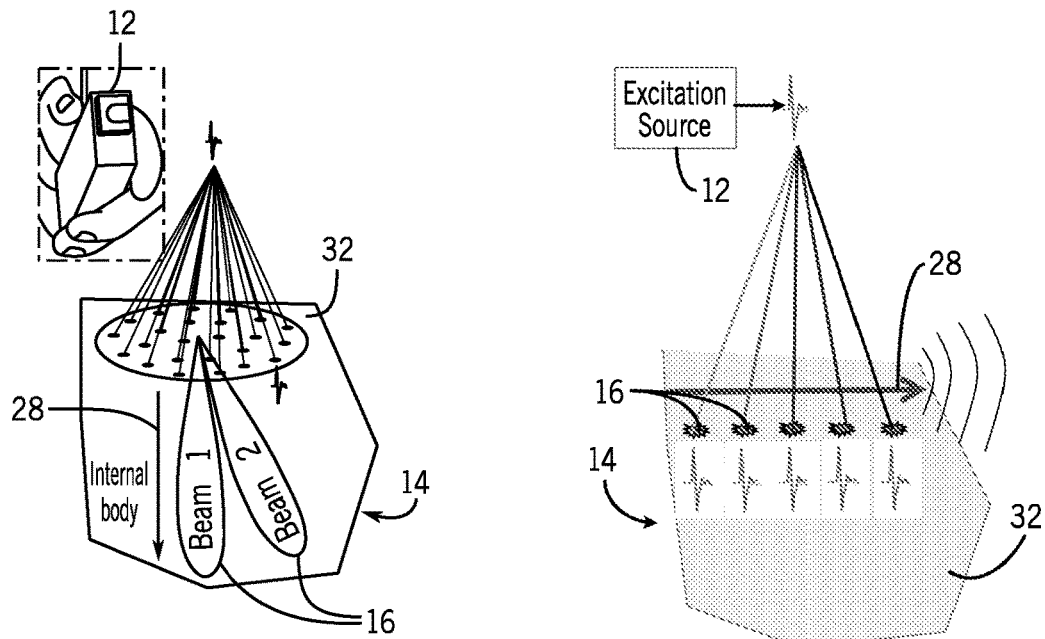
FIG. 3A
FIG. 3B

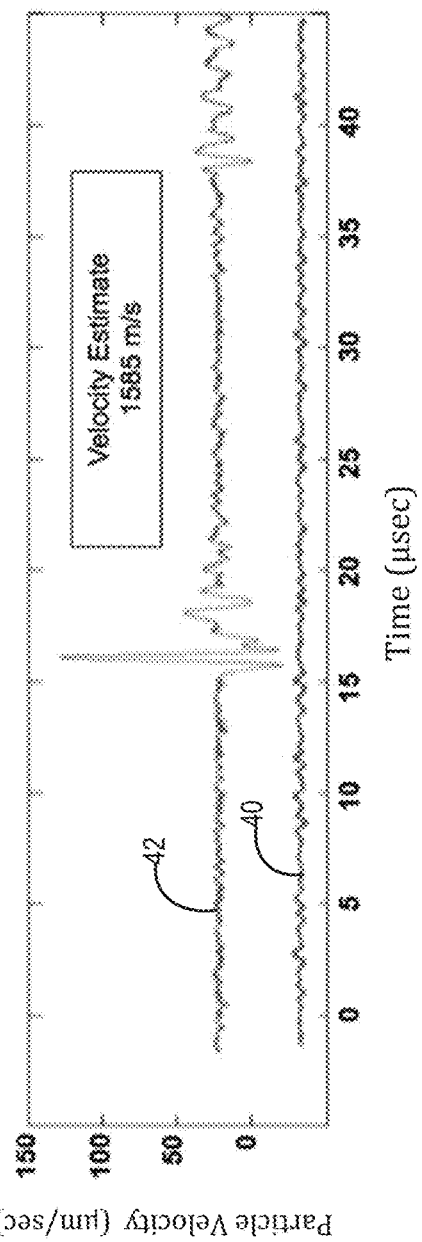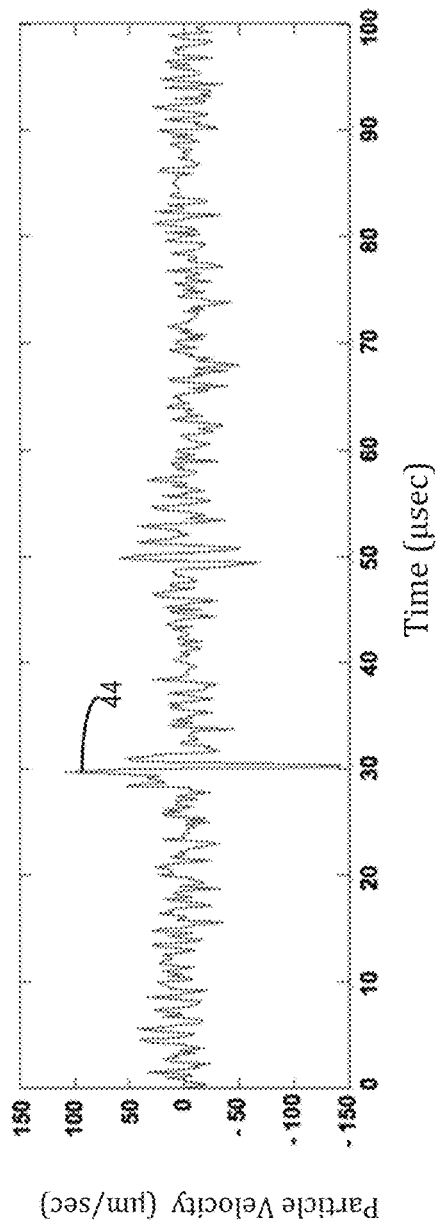
FIG. 5
FIG. 6

| Measurement Configuration | Excitation Source | Signal Sensor Receiver | Measured SNR (dB) |
|---|---|---|---|
| Full sample contact | 1 MHz longitudinal piezoelectric transducer | 1 MHz longitudinal piezoelectric transducer | 39 |
| Contact excitation/ optical measurement | 1 MHz longitudinal piezoelectric transducer | 2.5 MHz Polytec LDV (reflexite bead surface treatment) | 32 |
| Total optical, no contact | 355 nm; 10 nS optical pulse | 2.5 MHz Polytec LDV (reflexite bead surface treatment) | 37 |
| Contact excitation/ optical measurement | 1 MHz longitudinal piezoelectric transducer | 2 MHz MIT LL Custom LDV (no sample surface treatment) | 22 |
| Total optical, no contact | 355 nm; 10 nS optical pulse | 2 MHz MIT LL Custom LDV (no sample surface treatment) | 19 |

FIG. 8

SYSTEMS AND METHODS FOR GENERATING NON-CONTACT ULTRASOUND IMAGES USING PHOTOACOUSTIC ENERGY

CROSS-REFERENCE TO RELATED APPLICATIONS

This application is based on, claims priority to, and incorporates herein by reference in its entirety U.S. Provisional Application Ser. No. 61/907,843, filed Nov. 22, 2013, and entitled, "SYSTEM AND METHOD FOR NON-CONTACT ULTRASOUND."

STATEMENT REGARDING FEDERALLY SPONSORED RESEARCH

This invention was made with government support under FA8721-05-C-0002 awarded by the Air Force Life Cycle Management Center. The government has certain rights in the invention.

BACKGROUND OF THE INVENTION

The present invention relates to systems and methods for generating ultrasound images, and more particularly to systems and methods for generating ultrasound images without system contact to the patient, which may be achieved, for example, using photoacoustic energy and/or laser vibrometry.

Ultrasonic imaging techniques of body tissue and bone are well established in medical practices and aid physicians diagnosing diseases and injuries. Current systems rely on mechanical transducers and receivers in contact with the skin where coupling gels act as an interface to reduce the impedance between the device and skin. Conventional ultrasound images are obtained in a contact manner by using an ultrasonic transducer placed directly on the area of interest to send and receive the acoustic signals. In general, an acoustic pulse is emitted into to the body. Echoes from structures inside the body are reflected back to the transducer with the time of arrival providing information about the range to the structure. The acoustic source is omnidirectional, thus only range information is obtained, and a two-dimensional (2D) image is formed by using a line of transducers that yield information in the cross range direction.

However, considerable work is currently ongoing to form three-dimensional images via the scanning of the transducer line array. However, this presents registration error challenges as the individual 2D images must be aligned properly. Investigations are also ongoing to combine the individual source elements of 2D arrays of transducers in such a way that the transmitted energy has a directionality to obtain better quality spatial information. However, practical implementation of 2D arrays suffer from challenges in making a sufficiently large array that is conformal and uniformly coupled to the surface of interest (e.g. the human body).

Additionally, in certain circumstances, a noncontact operation for obtaining ultrasound images may be desirable. For example, in surgical situations where sterility is an issue, situations where direct contact is unpleasant or painful (e.g., imaging the eye), or emergency situations where the patient is in transit and/or being stabilized and may not be easily imaged via a contact system. Additional applications include, for example, real-time surgical feedback imaging, traumatic brain injury (TBI) detection, and bone health monitoring. Real-time surgical guidance and feedback could be improved from an imaging technique that can directly access exposed skin or traumatized tissue without contact, especially in very delicate procedures such as spinal and neck surgery.

One example approach includes photoacoustic tomography (PAT) which is an emerging optical technique. PAT is often used to image near surface shallow capillaries in animal tissue, for example, with typical penetration depths less than 1 mm. The PAT technique employs an optical source to cause the photoacoustic effect and contact transducers to record the response. Recent studies are exploring the laser Doppler vibrometer as a sensing device, thus making the system optical. In these studies, measureable signals are observed to depths of less than 1 cm in biological phantoms or natural tissue. However, for optical measurement systems to compete with practiced medical ultrasound, penetration depths of at least several inches are needed to probe structures of interest and, the light must be eye and skin safe.

Thus, there is a need for systems and methods capable of providing an efficient means for coupling acoustic energy into media in a noncontact manner to generate ultrasound images and, thereby, treatment of injuries such as TBI and bone fractures.

SUMMARY OF THE INVENTION

The present invention overcomes the aforementioned drawbacks by providing a non-contact ultrasonic imaging device. The present invention may use a laser imaging system that provides an acoustic amplitude that is significantly larger than that induced via standard photoacoustic means. Coherent summation of the propagating acoustic and/or elastic waves is achieved by scanning the laser source along the surface of the body at the speed of sound. The present invention may also use an array of vibrometer detectors to determine the mechanical modulus of the surface of a patient's skin.

The present invention provides a method for generating ultrasound images of a patient. The steps of the method include directing a photoacoustic excitation source into a scanning mirror to transmit acoustic disturbances into the patient to induce propagating photoacoustic waves. The plurality of acoustic and/or elastic disturbances are translated along the patient in a defined direction to cause a coherent summation of the propagating photoacoustic waves. The coherent summation generates a resultant wave that propagates along the defined direction to probe structures within the patient. Vibrations are detected at a surface of the patient created by backscatter of the resultant wave from the structures within the patient. Ultrasound images of the structures within the patient are then generated using the vibrations previously detected at the surface of the patient.

The present invention also provides a system for generating ultrasound images of a patient. The system includes a photoacoustic excitation source directed into a scanning mirror to transmit acoustic disturbances into the patient to induce propagating photoacoustic waves. The system also includes a sensor configured to detect vibrations at a surface of the patient created by backscatter of a resultant wave. A data acquisition system is configured to receive the resultant wave. The system also includes a processor that has access to the data acquisition system to translate the acoustic disturbances along the patient in a defined direction to cause a coherent summation of the propagating photoacoustic waves. The coherent summation results in the resultant wave that propagates along the defined direction to probe structures within the patient. The processor then measures the vibrations at the surface of the patient created by backscatter of the resultant wave from the structures within the patient. The processor then generates ultrasound images of the structures within the patient using the vibrations detected at the surface of the patient.

The present invention also provides a method for generating ultrasound images of a patient. The steps of the method include directing a laser source configured to produce a laser beam toward the patient to induce propagating photoacoustic waves. The laser beam is then translated along the patient in a defined direction to cause a coherent summation of the propagating photoacoustic waves and, thereby, a resultant wave that propagates along the defined direction to probe structures within the patient. Vibrations are detected, using a laser vibrometer sensing array, at a surface of the patient created by backscatter of the resultant wave from the structures within the patient. Ultrasound images of the structures within the patient are then generated using the vibrations detected at the surface of the patient.

The present invention also provides a system for generating ultrasound images of a patient. The system includes a laser source configured to produce a laser beam directed towards the patient to induce propagating photoacoustic waves. The system also includes a laser vibrometer sensing array configured to detect vibrations at a surface of the patient created by backscatter of a resultant wave. A data acquisition system configured to receive the resultant wave. The system also includes a processor that has access to the data acquisition system to translating the laser beam along the patient in a defined direction to cause a coherent summation of the propagating photoacoustic waves and, thereby, the resultant wave that propagates along the defined direction to probe structures within the patient. The processor may also be configured to measure the vibrations, using the laser vibrometer sensing array, at the surface of the patient created by backscatter of the resultant wave from the structures within the patient. The processor may then generate ultrasound images of the structures within the patient using the vibrations detected at the surface of the patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2 is an image showing an excitation source and sensing array configured to be implemented into the system of FIG. 1.

FIG. 3A is a diagram showing an excitation source to be implemented into the system of FIG. 1.

FIG. 3B is a diagram showing another excitation source to be implemented into the system of FIG. 1.

FIG. 5 is a graph showing particle velocity over time of a photoacoustically induced elastic wave through a tissue sample utilizing a conventional laser vibrometer.

FIG. 6 is a graph showing particle velocity over time of a photoacoustically induced elastic wave through a tissue sample utilizing the system of FIG. 1.

FIG. 8 is a table showing signal-to-noise-ratio (SNR) comparisons for contact and optical ultrasonic measurement systems.

DETAILED DESCRIPTION OF THE INVENTION

As will be described, the present invention includes a variety of systems and methods that may be used alone or in combination. For example, one component described hereafter includes a system for using photoacoustic excitation phenomena to generate propagating elastic waves into the body that can then reflect, refract, scatter, and absorb off interior structures. In this regard, a non-contact photoacoustic excitation source is provided that can steer the ultrasonic elastic wave beam as desired into the body. These elastic waves then propagate back to the skin surface, where they are measured and used to facilitate analysis of the body.

Another component described hereafter includes a non-contact laser vibrometer or a non-contact digital focal plane array (DFPA), which can be used to provide a flood illumination of the skin surface. In this regard, the vibrometer or DFPA system can be used to measure the above-referenced elastic waves or can be used separately for other purposes. In the case of measuring returns of the above-described elastic wave, the returns can be processed and constructed to form a reflection image of the body interior based on elastic wave impedance contrast. The vibrometry and/or DFPA sensing devices can provide motion compensation capabilities for a static or moving detector platform or a static or moving subject that enables a resolved image. Without these capabilities, the return signal is not resolvable for moving systems.

The photoacoustic effect may be used as a means to couple acoustic energy into a human subject. The photoacoustic effect is a well-known process by which optical energy, typically from a laser, is absorbed by a medium. This transfer of energy results in a thermal expansion of the medium, which will result in a propagating acoustic and/or elastic wave. Many of the properties of the resulting acoustic and/or elastic wave can be controlled by the source laser within the material limitations of the source medium. Using a laser system eliminates coupling gels that are conventionally used in ultrasound imaging and applied to the patient's skin that can contaminate open body tissues. In addition, a laser system can provide fine spatial and temporal resolution to yield higher quality images while reducing distortion observed with contact sensing deformation. Biomedical photoacoustic systems can use laser wavelengths in the visible to near infrared (i.e., 400-1100 nm), which have absorption depths of approximately 0.1-10 cm. However, the actual penetration depth is usually less than the absorption depth due to significant optical scattering. In addition, existing photoacoustic systems utilize a single source of optical illumination with a fairly weak resultant acoustic response, making it difficult to probe structures within the patient.

Figure 1:
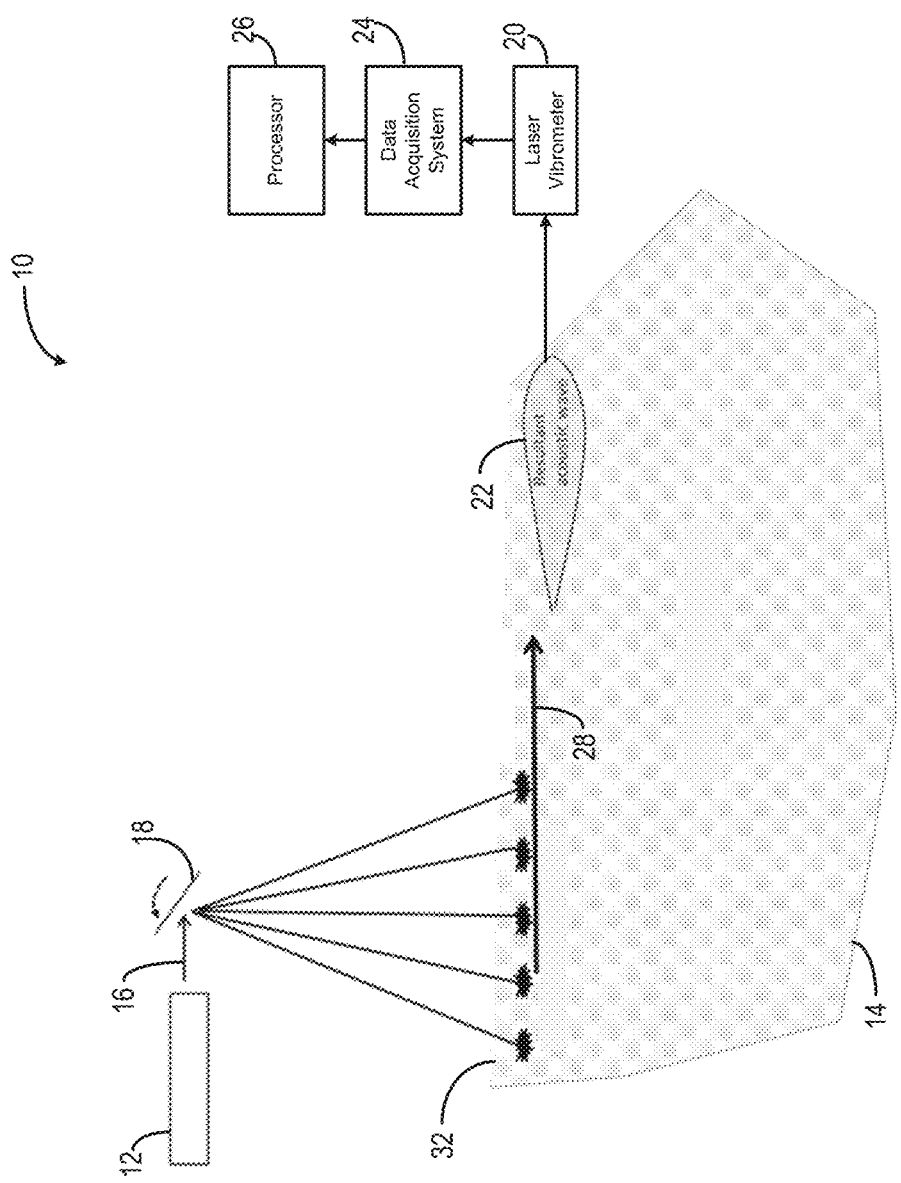
FIG. 1 is an schematic diagram showing a system configured to implement the present invention for generating ultrasound images.

Referring now to FIGS. 1 and 2, a system 10 is shown that provides a means to propagate acoustic energy in a single direction so that the acoustic amplitude can be larger than that induced via standard photoacoustic means. The system 10 may include a photoacoustic excitation source 12 configured to transmit acoustic disturbances into a patient 14 to induce propagating photoacoustic waves. The photoacoustic excitation source 12 may be, for example, a directed source of radio frequency energy or microwave energy. Alternatively, the photoacoustic source 12 may be a handheld device, such as a laser source configured to produce a modulating frequency between about 0 Hz to 10 MHz. Likewise, the photoacoustic source 12 may be a continuous wave (CW) laser. The photoacoustic source 12 may be arranged remotely from the patient 14 and produce a laser beam 16 directed at a scanning mirror 18 to transmit the acoustic disturbances into the patient 14. A sensor 20, for example, a laser vibrometer sensing array or an ultrasonic transducer receiver, may be positioned remotely from the patient 14 to detect vibrations created by backscatter of a resultant wave 22, as shown in FIG. 1. The resultant wave 22 may be generated by a coherent summation of the propagating photoacoustic waves. A data acquisition system 24, as shown in FIG. 1, may be coupled to the sensor 20 to receive the resultant wave 22 and a processor 26 may be coupled to the data acquisition system 24.

As shown in FIG. 1, the processor 26 may be configured to translate the acoustic disturbances along the patient 14 in a defined direction 28, as indicated by the arrow in FIG. 1, by rotating either the scanning mirror 18 or translating the photoacoustic excitation source 12 such that the laser spot incident upon the patient moves at the speed of sound, for example. This translation results in the coherent summation of the propagating photoacoustic waves to produce the resultant wave 22. The beam 16 is moved along the defined direction 28. For example, the mirror 18 may be moved to thereby move the beam 16 along the defined direction 28. Also, though more cumbersome, the source 12 can be moved. The processor 26 may also be configured to measure the vibrations at a surface 32 of the patient 14. The vibrations are created by the backscatter of the resultant wave 22 from probing the structures within the patient 14. The processor 26 may then generate ultrasound images of the structures within the patient using the vibrations detected by the sensor 20.

Referring now to FIG. 3A, the photoacoustic excitation source 12 is shown as a handheld laser source. The handheld laser source may be used to generate elastic wave propagation into the body. The non-contact laser excitation source generates acoustic/ultrasonic waves that travel into the patient 14 and return back to the skin surface 32. The laser source may be timed/phased to transmit the laser beam 16 that propagates in the defined direction 28 in order to scan the structures of the patient 14 at locations deeper than the optical penetration depth. The laser source may be, for example, a low-powered laser system that can generate acoustic/ultrasonic bandwidths and power levels that propagate into the patient 14, return to the skin surface 32, and that can be readily used to form ultrasound images. Thus, the laser source provides a controlled directional source of acoustic energy to probe and image specific structures of the patient 14. Advantageously, the acoustic and/or elastic waves have a directionality that eases the ability to generate three-dimensional ultrasound images.

Alternatively, as shown in FIG. 3B the photoacoustic excitation source 12 may be translated along the patient 14, for example, at the speed of sound, in a defined direction to cause a coherent summation of the propagating photoacoustic waves. The coherent summation of the propagating photoacoustic waves results in generation of a directional resultant wave. Coherent summation of the propagating photoacoustic waves has the advantage that the wave amplitudes, rather than intensities, add, leading to a stronger overall resultant wave. The resultant wave may propagate along the defined direction to probe structures of the patient's 14 body.

Referring back to FIGS. 1 and 2, once the photoacoustic excitation source 12 is used to induce the propagating photoacoustic waves into the patient 14, the waves scatter, reflect, and refract in relation to the tissue mechanical property contrasts. As the propagating photoacoustic waves are backscattered towards the surface 32, vibrations are induced at the surface 32. The vibrations may be detected and measured remotely without contacting the patient 14 using the sensor 20 (i.e., the laser vibrometer sensing arrays). The sensor 20 operates as interferometer, for example, that emits a beam of light configured to be safely delivered to an eye or skin of the patient 14. The sensor 20 may be for example, a Coherent Multipixel Imaging system or a Digital Focal Plane Array (DFPA). The sensor 20 receives the spatially distributed acoustic/ultrasonic return from the body interior. These signals are then processed by the processor 26, as shown in FIG. 1, to form structural 2D and 3D ultrasound images of the interior structures of the patient 14.

The sensor 20 can measure vibrations over a frequency band from 1 Hz ranging to 40 MHz, for example. The sensor 20 may include firmware, for example, that utilizes Doppler tracking to compensate for movement of the patient 14. Further, the sensor 20 may provide motion-compensation capabilities that enable measurement of transmitted elastic waves in the body from a moving reference such as the handheld laser source 12, as shown in FIG. 3A. Thus, elastic wave excitation and measurement can be performed from as little as a few inches away from the patient 14 to as much as 30 meters, for example, from the patient 14.

In one non-limiting example, the photoacoustic excitation source 12 may be an optical source configured to generate acoustic and elastic waves in the body of the patient 14 from a standoff—noncontact position. More specifically, the optical source may generate a short optical frequency pulse to initiate and generate ultrasonic waves into tissue of the patient 14, which are driven by the primary mechanism of photoacoustic phenomena. Photoacoustic phenomena first develop from the photons that impinge on a target surface emitted from an optical source and the conversion of the photons into heat by the absorbing material, such as a fluid or biological tissue complex. This process may be a non-linear thermal shock loading that enables low Q tissue to deform rapidly and thus, generates ultrasonic acoustic and elastic waves.

In a first stage of the photoacoustic process, photons are absorbed by particles comprising a tissue volume, where the absorption coefficient $\mu_a$ is described below by equation (1):

$$\mu_a = \rho \sigma_a \text{ where, } \sigma_a = -4\frac{2\pi a}{\lambda}\pi a^2 \text{Im}\left\{\frac{n_1 - n_0}{n_1 + 2n_0}\right\} \qquad (1)$$

where $\rho$ and $\sigma_a$ are the particle density and cross-sectional area, respectively, and a is the particle radius, where a<<the optical wavelength, and $n_1$ and $n_0$ are the refraction indicies, respectively, of the absorbing material and an infinite homogeneous non-absorbing medium.

For an optical pulse incident on tissue particles, the total absorbed energy, $E_a$ may be described according to equation (2) below:

$$E_a(r,t) = \mu_a \int_{4\pi} I(r,t,\hat{s}) d\Omega = \mu_a U^{inc}(r,t) \qquad (2)$$

Where I is the specific intensity absorbed by the tissue particles at a position r from light incident in a direction $\hat{s}$. $U^{inc}$ may be the average incident intensity with units of J/cm$^2$. The average incident intensity may be of particular concern when developing an optical laser ultrasound where the intensity is within eye and skin safe limits for the duration of optical radiation. In one example, 1-20 mJ/cm$^2$ is likely to meet safety requirements in the operational system 10.

The governing relationship establishing tissue deformation and thus, acoustic or elastic wave generation evolves from the tissue temperature increase caused by the absorbed energy as shown in equation (3) below:

$$\rho_m C \frac{\partial T(r,t)}{\partial t} - \kappa \nabla^2 T(r,t) = E_a(r,t) \qquad (3)$$

Where $\rho_m$, C, $\kappa$, T are the tissue mass density, specific heat, thermal conductivity, and temperature, respectively. The first term shown in equation (3) describes the temperature increase due to optical absorption and diffusion. The optical diffusion may be several orders of magnitude larger than that of the thermal diffusion, thus, the second term shown in equation (3) may be negligible and the temperature increase due to the optical pulse radiation can be described by equation (4) below:

$$\frac{\partial T(r,t)}{\partial t} \approx \frac{1}{\rho_m C}\mu_a U^{inc}(r,t) \qquad (4)$$

In addition, equation (4) may imply that thermal diffusion can be neglected since the optical pulse duration is considerably smaller than the time scale of thermal diffusion.

The effect of optical propagation into a scattering media, such as complex biological tissues, may be another component to understanding the process of photoacoustic phenomenology. Typically, the materials comprising tissue mass are considerably heterogeneous, where blood hemoglobin, for example, is highly absorptive to light while other tissue cells are simultaneously, highly reflective. Light and optical frequency waves may propagate in tissue and can be described by a diffusion approximation as shown in equation (5) below. The diffusion of the optical average intensity, U due to an incident energy density, $S_0$ is as follows:

$$D\nabla^2 U(r,t) - \frac{1}{c}\frac{\partial U(r,t)}{\partial t} - \overline{\mu_a}(r)U(r,t) = -S_0(r,t) \qquad (5)$$

In equation (5) above, D may be the optical diffusion coefficient and c may be the average speed of light in the tissue. The average intensity experienced in a homogeneous scattering tissue column can then be related to the average incident energy as a function of frequency according to equation (6) below:

$$\tilde{U}(r,\omega) = \tilde{U}^{inc}(r_s,r) + \frac{1}{4\pi}\int_V \tilde{U}^{inc}(r_s,r')\Delta\mu_a(r') \times g(\gamma_0|r-r'|)dr' \qquad (6)$$

In equation (6) above, g may be a 3D Green's function, for example, and $\gamma_0$ may be the frequency-dependent wave number for the optical diffuse photon density wave. The average incident energy can be derived showing the relationship between the incident energy density in the time domain according to equation (7) below:

$$U^{inc}(r_s,r,t) = \frac{s_0}{(4\pi Dct)^{3/2}}\exp\left[\frac{|r_s-r|}{4Dct} - \mu_a|r_s-r|\right] \qquad (7)$$

The acoustic or elastic wave that can be measured by the sensor 20, such as an optical receiver including a laser Doppler vibrometer or conventional contact transducer, is another component to describing photoacoustic conversion of light to pressure and resultant acoustic wave propagation. For simplicity, an inviscid fluid may be used to demonstrate the generation and propagation of the longitudinal or compressional wave from incident light, as shown in the linear force equation (8) below:

$$\rho_m \frac{\partial^2 u(r,t)}{\partial t^2} = -\nabla p(r,t) \qquad (8)$$

where u may be the acoustic displacement and p may be the acoustic pressure. The tissue media may then deform from expansion according to equation (9) below:

$$\nabla \cdot u(r, t) = -\frac{p(r, t)}{\rho_m v_s^2} + \beta T(r, t) \qquad (9)$$

where $\beta$ is the volume expansion coefficient and $v_s$ is the acoustic speed in the tissue.

$$\nabla^2 p(r, t) - \frac{1}{v_s^2}\frac{\partial^2 p(r, t)}{\partial t^2} = \rho_m \beta \frac{\partial^2 T(r, t)}{\partial t^2} \qquad (10)$$

Combing equations (9) and (10) above, the relationship between the heat source and the resultant pressure is shown below in equation (11) in terms of the optical average intensity and optical absorption coefficient:

$$\nabla^2 p(r, t) - \frac{1}{v_s^2}\frac{\partial^2 p(r, t)}{\partial t^2} = \frac{\beta}{C}[\mu_a + \Delta\mu_a(r)]\frac{\partial U(r, t)}{\partial t} \qquad (11)$$

The pressure distribution along the tissue column resolves to equation (12):

$$p(r, t) = p_0(r, t) + \frac{\beta}{4\pi C}\int_V \frac{dr'}{|r-r'|}\Delta\mu_a(r') \times \left|\frac{\partial U^{inc}(r', t')}{\partial t'}\right|_{t'=t-\frac{|r-r'|}{v_s}} \qquad (12)$$

Where $$p_0(r, t) = \frac{\beta\mu_a}{4\pi C}\int_V \frac{dr'}{|r-r'|}\left|\frac{\partial U^{inc}(r', t')}{\partial t'}\right|_{t'=t-|r-r'|/v_s}$$

In equation (12) above, $p_0(r, t)$ may be the incident pressure at the onset of the tissue column.

Once the photoacoustic excitation source 12 described above transmits acoustic disturbances into the patient 14, the sensor 20, such as a noncontact laser vibrometer sensing array, may measure the ultrasonic returns. The ultrasonic returns may be stimulated by the optical excitation sources that arrive from internal boundaries composing structures and material property distributions inside the patient 14, for example. In one non-limiting example, the sensor 20 is an optical heterodyne ladar design utilized for the vibrometer sensing system.

In conventional heterodyne detection, a signal of interest at a known frequency is non-linearly mixed with a reference "local oscillator" (LO) that is set at a close-by frequency. The desired outcome may be the difference frequency, which carries the signal information (i.e., amplitude, phase, and frequency modulation) of the original higher frequency signal, but is oscillating at a lower more easily processed carrier frequency. Electrical field oscillations in the optical frequency range cannot be directly measured since the relatively high optical frequencies have faster oscillating fields than electronics can respond. Instead, optical photons are detected by energy or equivalently by photon counting, which are proportional to the square of the electric field and thereby form a non-linear event. Thus, when the LO and the signal beams impinge together on a target surface, such as the surface 32 of the patient 14, the LO and signal beams "mix" and produce heterodyne beat frequencies.

The performance of a laser vibrometer, for example, and the process of ultrasonic wave measurement may be determined by the noise floor of the laser vibrometer. The noise floor may include, but is not limited to, 1) shot noise that dominates the noise floor at ultrasonic frequencies, 2) speckle noise that contributes noise in the audible acoustic band, and 3) platform and subject target vibration caused by motion by a variety of potential sources other than the intended system optical excitation source.

Shot noise may arise from statistical fluctuations in measurements. The detected electrical current for a heterodyne ladar may be described according to equation (13) below:

$$i(t)=i_{LO}+i_s(t)+2\sqrt{\eta_h i_{LO} i_s(t)}\cos[\omega_{IF}t+\theta(t)] \qquad (13)$$

where $i_{LO}$ and $i_s(t)$ are the currents from the local oscillator and signal, $\eta_h$ is the heterodyne mixing efficiency (0 to 1), $\omega_{IF}$ is the intermediate frequency (carrier signal is mixed with the local oscillator to produce a difference or beat frequency to improve signal gain), and $\theta(t)$ is the phase shift. $\omega_{IF}$ is equal to the acousto-optic modulator frequency offset plus the Doppler offset due to platform motion. Thus, the phase shift may be described according to equation (14) below:

$$\theta(t) = 2kx(t) + \theta_s(t) = \frac{4\pi x(t)}{\lambda} + \theta_s(t) \qquad (14)$$

where x(t) is the line-of-sight distance between the heterodyne ladar and tissue surface 32, $\theta_s(t)$ is the random phase of the speckle lobe, and $\lambda$ is the optical wavelength of the laser vibrometer. x(t) may change due to body vibrations and movement, laser platform vibration, and pointing jitter, for example.

The laser vibrometer sensing arrays 20 may be characterized by the carrier-to-noise ratio (CNR). More specifically, the received number of photoelectrons per second, $\phi_e$ (i.e., optical return from the vibrating tissue surface) over the vibrometer demodulated bandwidth may determine the received signal quality. The greater the number of photoelectrons received by the laser sensing system, for example, the lower the shot noise is, thus, resulting in a more sensitive laser vibrometer 20. In some embodiments, the CNR may be increased by increasing the power of the laser vibrometer 20 and by decreasing the laser beam 16 diameter that impinges upon the tissue surface 32.

The shot noise spectrum of the surface particle velocity, $A_{v,sh}$ as a function of frequency, f, may be proportional to the received returning photoelectrons as described by equation (15) below:

$$A_{v,sh}(f) = \frac{f\lambda}{\sqrt{\phi_e}} \qquad (15)$$

As previously described, another source of noise may be from speckle, for example. Speckle is the noise that occurs due to the distribution of optical scatters on the tissue surface 32 encountered by the laser beam 16. For a diffuse surface, for example, there may be many scatterers (based on surface roughness) that reflect light back to the receiver. The speckle noise contribution to the laser vibrometer 20 can be reduced by signal time integration with respect to the same realization of scatterers. Increasing the integration time may reduce speckle noise and thus improve the sensitivity of the system 10. However, if during the allotted integration summing time, the laser beam 16 changes position on the target surface 32 due to platform motion, beam jitter, or target movement, for example, the speckle realization may change thereby creating translation or dynamic speckle and increase in the noise floor. Faster laser beam 16 translation speeds across the surface 32 of the patient 14 may also increase the speckle noise floor contribution. The speckle noise amplitude may be described according to equation (16) below:

$$A_{v,sp}(f) = \lambda \sqrt{\frac{\pi f_{exc}^2}{12}} \sqrt{\frac{2\alpha}{\alpha^2 + (2\pi f)^2}} \quad (16)$$

where $a = 2\pi f_{exc}$ and $f_{exc} = v_t/d$ (i.e., laser beam translation velocity on target over the laser beam diameter) is the exchange rate of the speckle pattern.

Figure 4:
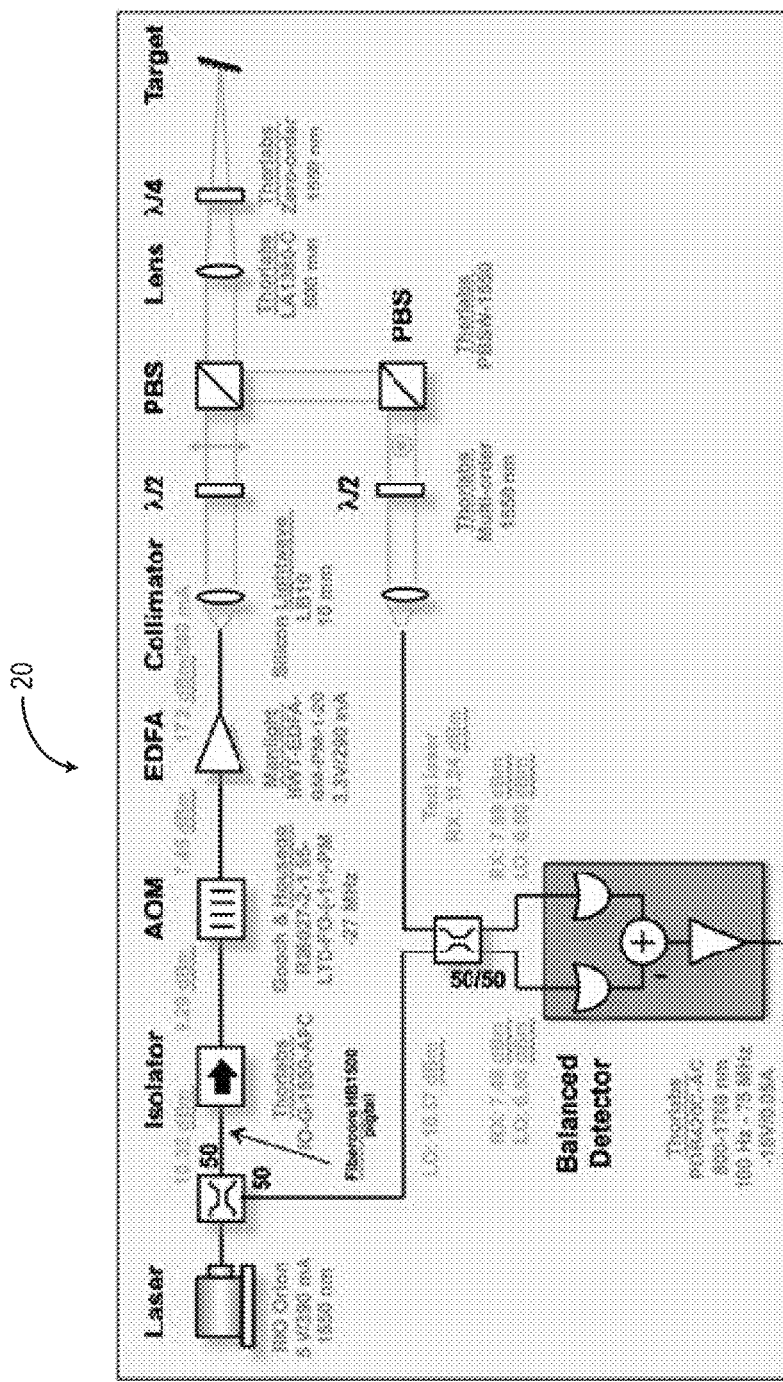
FIG. 4 is a diagram showing a laser Doppler vibrometer system configured to be implemented into the system of FIG. 1.

Performance of the laser vibrometer, such as the laser Doppler vibrometer 20 shown in FIG. 4, for ultrasonic measurements may be characterized by the shot noise contribution (e.g., at 1 MHz), for example, that is anticipated to dominate the noise floor sensitivity. However, when introducing system motion, speckle noise may become a significant factor. Even subtle motion with a small laser beam 16 diameter (on the order of millimeters) can produce significant fluctuations in the speckle realization and resultant noise floor.

In order to measure ultrasonic signals generated from the optical photoacoustic excitation source 12 utilizing the laser vibrometer 20, the system 10 may undergo a series of tests. The end result measurements from the series of tests may, in some embodiments, be conducted without coupling gels or reflexite beads for laser return enhancement or other means. The signal quality generated using the present laser vibrometer 20 may be compared to a commercial laser vibrometer, such as the laser vibrometer manufactured by Polytec, Inc., and contact ultrasonic transducers manufactured by Olympus, for example.

In a first set of transmission measurements, the direct acoustic/elastic wave transmission for through tissue samples may be measured with the laser Doppler vibrometer 20 or conventional contact ultrasonic receiving transducers. The optical source utilized may be a Continuum Q-switched 15 pulse/sec laser, for example, operating at about a 355 nm with pulse energies at the sample surface of 1-4 mJ and a spot size of 0.05 cm² yielding fluencies per pulse of 20-80 mJ/cm². The laser vibrometer beam (sensing receiver) may be aimed on an opposing side of the tissue sample, but co-located with the excitation laser beam 16. The tissue sample may be about one inch thick. Received signals measured using the laser vibrometer 20 may be recorded using the data acquisition system 24 of FIG. 1, for example. The data acquisition system 24 may include, as one example, an Agilent Technologies L4534A 20 M sample/sec digitizer. The contact transducer received signal and commercial laser vibrometer (i.e., Polytec, Inc. laser vibrometer) measurements may be recorded on a Tektronix TDS 2024B digital oscilloscope, for example.

In the present example, the laser Doppler vibrometer (LDV) 20 may be positioned about five feet from the tissue sample. The laser source 12, such as a Q-switched laser, is placed about one foot from the tissue sample, to initiate ultrasonic waves into the tissue sample via photoacoustic mechanisms. This configuration allows for a direct elastic wave transmission through the tissue sample. Referring to FIG. 5, the LDV measurement of direct elastic wave transmission through the tissue sample is shown using the LDV sensor. A first curve 40 shows the LDV measured response of the photoacoustically induced elastic wave when the Q-switched laser pulse is blocked with a metal plate between the excitation source and the tissue sample. A second curve 42 shows the response due to elastic wave transmission when the source beam is unimpeded. Thus, reflexite glass beads (~1 μm diameter) were necessary to achieve a reasonable SNR to detect the return signal from the surface of the tissue sample. Without the reflexite glass beads, the signal was unobservable.

However, using the present laser vibrometer 20, measurement of the direct transmission is achievable without reflexite dust. The laser vibrometer 20 achieved a better SNR due to a higher optical power of about 45 mW with a 1550 nm wavelength compared to the commercially available Polytec vibrometer power of 2 mW and 633 nm wavelength. With reference to equation (15) above, the laser vibrometer 20 may achieve a shot noise floor reduction by a factor of two better than the Polytec laser vibrometer for equal spot sizes primarily due to higher power ($\lambda/\sqrt{power}$). In addition, signal processing gains in the laser vibrometer 20 may display improved performance over the Polytec vibrometer.

Turning now to FIG. 6, the signal return measurement using the laser vibrometer 20 without sample surface treatment is shown. More specifically, a first curve 44 shows the response from the LDV sensor measurement of direct elastic wave transmission through the tissue sample generated by optical frequency short pulse using Q-switched laser. In this measurement example, there are no reflexite beads or any substances used to treat the sample surface to reduce the LDV noise floor response. The direct wave transmission may be observed at about 30 microseconds, and the first reflection from the back of the tissue sample may be observed at about 50 microseconds.

Figure 7:
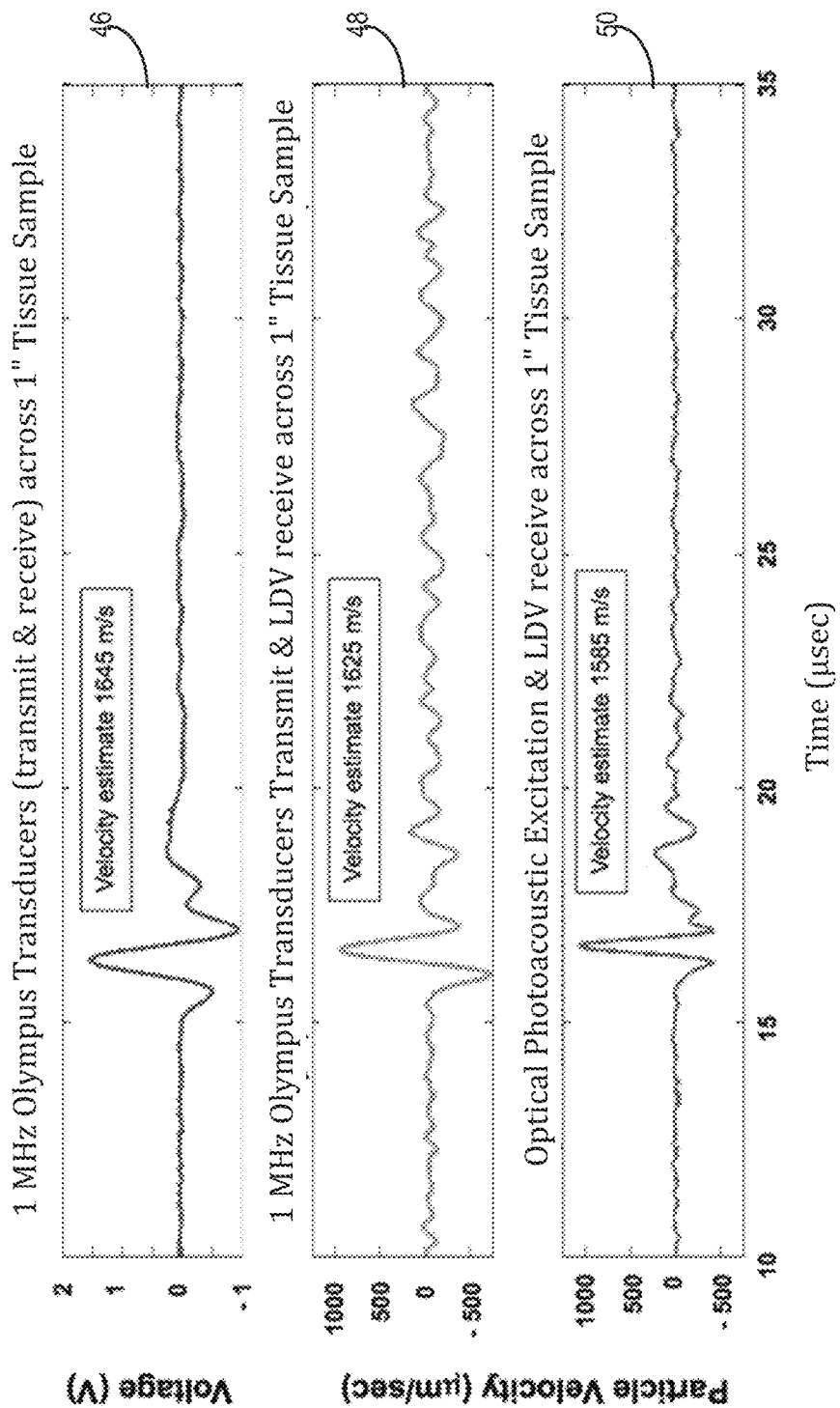
FIG. 7 is a series of graphs comparing elastic wave transmission through a tissue sample utilizing various excitation and sensor sources.

In one non-limiting example, the signal-to-noise-ratio (SNR) for combinations of contact transducers and optical devices for the direct transmission measurement configuration may be compared. As shown in FIG. 7, comparison of contact piezoelectric transducer and optical ultrasonic measurements are shown. The transmit pulse may be initiated at t=0. A first graph 46 shows the transducer transmit and receive system having direct elastic wave transmission through a one inch tissue sample in contact with and measured by a 1 MHz longitudinal transducer, for example. The contact ultrasonic source may be a 1 MHz longitudinal transducer. A second graph 48 shows the transducer transmit and LDV receive system having direct elastic wave transmission through a one inch tissue sample measured by the LDV beam pointed at the tissue sample. The ultrasonic source may be a 1 MHz longitudinal contact transducer. Lastly, a third graph 50 shows the optical transmit and LDV receive system utilizing total noncontact standoff optical ultrasound. Direct elastic wave transmission, as shown in the third graph 50 may be generated by a 355 nm Q-switched laser pulse and measured by the LDV beam pointed at an opposite side of the tissue sample, for example.

The SNR may be computed for each configuration as shown in the table of FIG. 8. The SNR may defined by equation (17) below:

$$SNR = 10\log_{10}\left(\frac{Ps^2 - Mn^2}{Vn}\right) \quad (17)$$

where Ps is the peak signal amplitude, Mn is the mean noise, and Vn is the variance of the noise. With continued reference to FIG. 8, SNR comparisons for contact and optical ultrasonic measurement approaches indicate that the contact transducer system provides a SNR and signal quality that are better than those of optical devices without any sample treatment. The SNR is comparable for the total contact transducer arrangement compared to total optical arrangement using the Polytec with reflexite bead sample treatment (to reduce its noise floor).

However, the use of gel and axial force to hold the transducers enables coupling and has may affect the SNR. In addition, holding contact transducers in place deforms the tissue sample, such that the mechanical and transmission properties of the tissue sample are modified compared to the natural state. The observed transmission velocity, as shown in FIG. 7, is 1645 m/s and may be over estimated compared to muscle longitudinal velocities reported in the literature of 1580 m/s. The total optical measurement velocity estimate is about 1585 m/s for the optical transmit and LDV receive system, shown in FIG. 7. Thus, in the case of the total optical measurement using the laser vibrometer 20 without surface treatment to reduce the vibrometer noise floor, the SNR is the lowest, as shown in FIG. 8, and may be influenced by the reduced confining pressure on the tissue sample.

Figure 9:
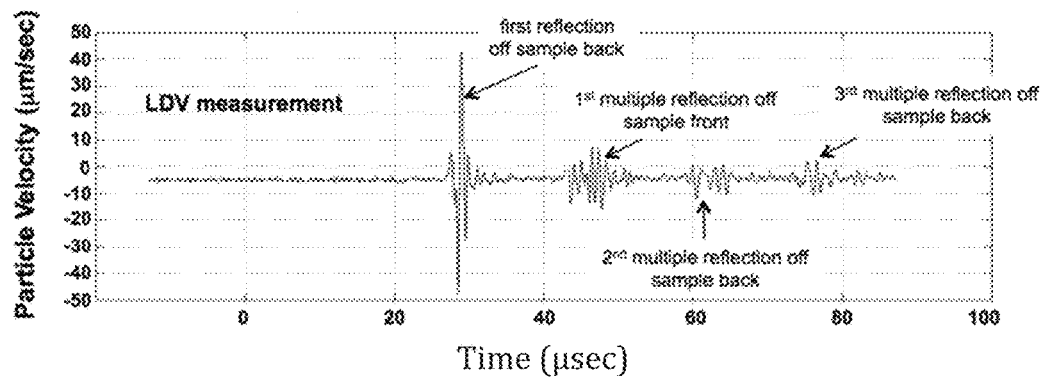
FIG. 9 is a graph showing particle velocity over time of reflected elastic wave transmission through a tissue sample for a total optical arrangement.

In another non-limiting example, a second series of measurements may be acquired by the optical excitation source 12 and laser vibrometer sensors 20. The total optical measurement configuration may be examined to analyze the reflection signal quality and probing depth of ultrasonic wave propagation. In these tests, the optical transmitter and optical sensing vibrometer may be located on the same side of the tissue sample, for example, which may be more common for use in ultrasonic imaging and probing. In one embodiment, the direct transmission configuration may be used for tomographic ultrasound imaging applications. Turning to FIG. 9, the LDV measurement of reflected elastic wave transmission through the tissue sample for the total optical arrangement where the transmitter and receiver are on the same side of the tissue sample is shown.

With continued reference to FIG. 9, the LDV and Q-switched laser are on the same side of the tissue sample. The excitation source and sensor beam spots may be approximately 0.5 inch apart on the tissue sample, and the elastic wave may be measured using the LDV sensor. The first reflected arrival from the back of the sample (i.e., tissue/air interface) shows the largest amplitude signal in FIG. 9. Subsequent multiple reflections may be observed with increasing time. The third multiple still shows a significant SNR which has experienced a travel path of four inches back and forth in the tissue sample.

Figure 10:
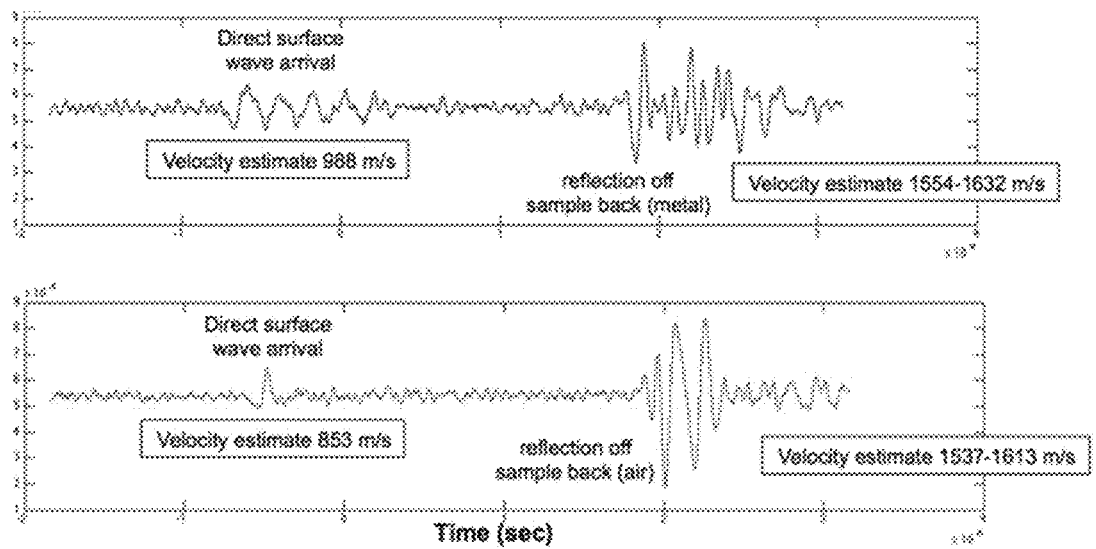
FIG. 10 is a pair of graphs showing reflected elastic wave transmission through a tissue sample utilizing a LDV measurement.

Referring now to FIG. 10, the contrast in reflection signal structure and quality for a one inch thick tissue sample is shown. In this arrangement, the Q-switched laser and LDV measure the signal from the same side of the tissue sample. The measured reflected elastic wave signal off a metal plate backing the tissue sample is shown in the top graph of FIG. 10. The metal plate is coupled to the tissue sample using a thin layer of Dow vacuum grease, for example. The signal for a tissue sample without metal backing is shown for comparison in the bottom graph of FIG. 10. The reflected signal may be attributed to the large impedance between the tissue and open air on the sample back. In both graphs of FIG. 10, the reflected signal character are noticeably different indicating that a finite plate backing the tissue sample may be imaged and mapped for different optical transmitter and sensing positions on the tissue sample face.

Figure 11:
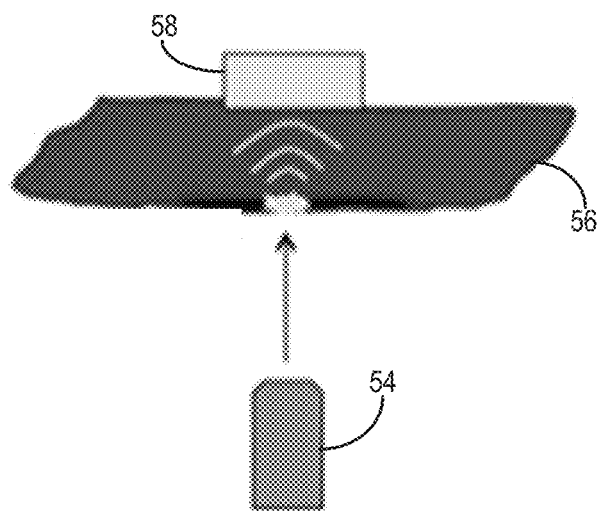
FIG. 11 is a diagram showing an example laser diode apparatus for transmitting single frequency acoustic tones utilizing an optical modulation onto a continuous wave optical carrier.

Referring now to FIG. 11, in another non-limiting example, a laser diode 54 may be used to stimulate acoustic and elastic waves in biological tissue 56 in place of the previously described Q-switched laser. The laser diodes 54 for photoacoustic excitation may include, for example, an opto-acoustic excitation source for a single channel and a line array 58. The excitation system shown in FIG. 11 may be capable of transmitting single frequency acoustic tones by employing a optical modulation onto a continuous wave optical carrier. A pulse compression technique may then be used to synthesize the acoustic-elastic wave short pulse from the received tones at the observation sensing position. A forcing function may be calculated at the source location using super position of each frequency tone over a 35 frequency chirp from about 222 kHz to about 909 kHz. Each acoustic—elastic wave tone may be measured on the opposite side of the tissue 56. Next, the measured tones may be processed using a narrow band filter, for example. Additionally or alternatively, each tone may then be summed in time to construct the short pulse.

Figure 12:
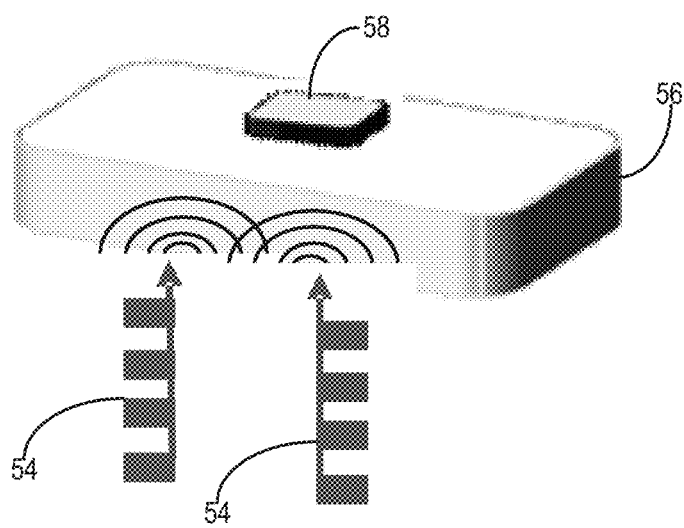
FIG. 12 is a diagram showing another example laser diode apparatus configured to transmit optically modulated carriers at continuous wave frequencies.
Figure 13:
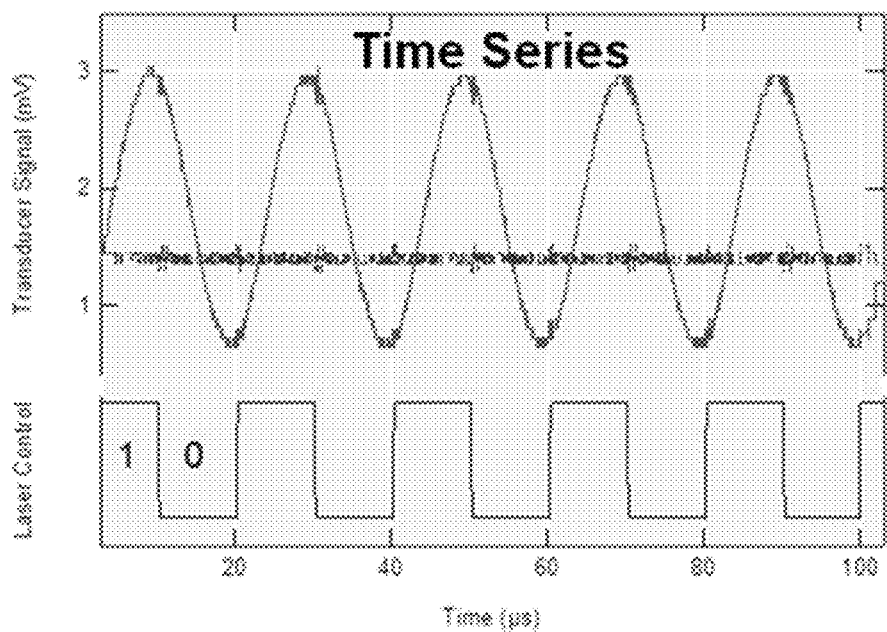
FIG. 13 is a time series graph showing a 50 kHz acoustic tone generated optically by modulating an optical carrier at a pulse repetition frequency of 50 kHz.
Figure 14:
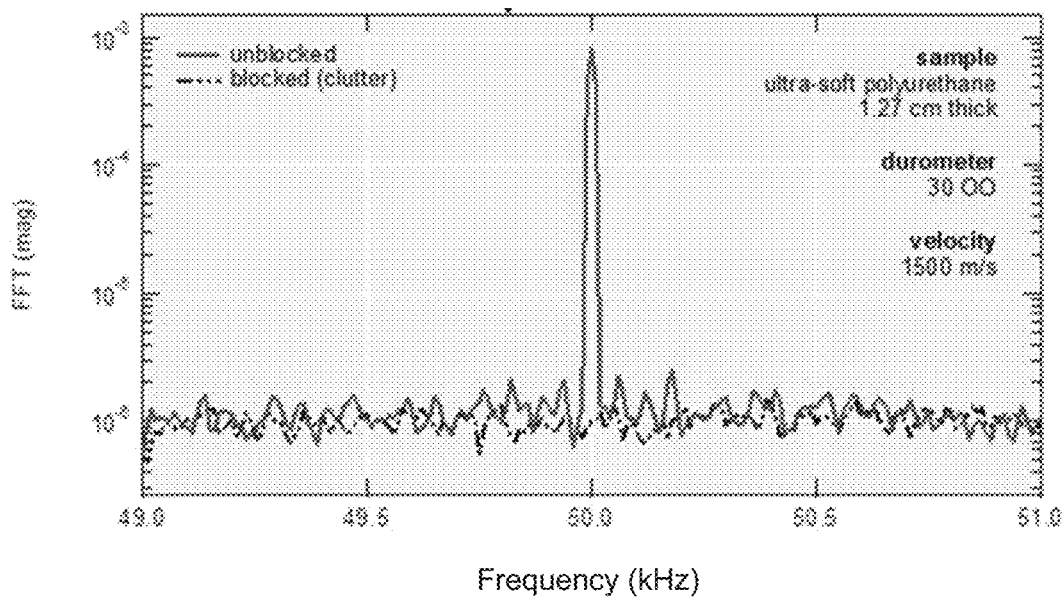
FIG. 14 a spectrum graph showing a 50 kHz acoustic tone generated optically by modulating an optical carrier at a pulse repetition frequency of 50 kHz.
Figure 15:
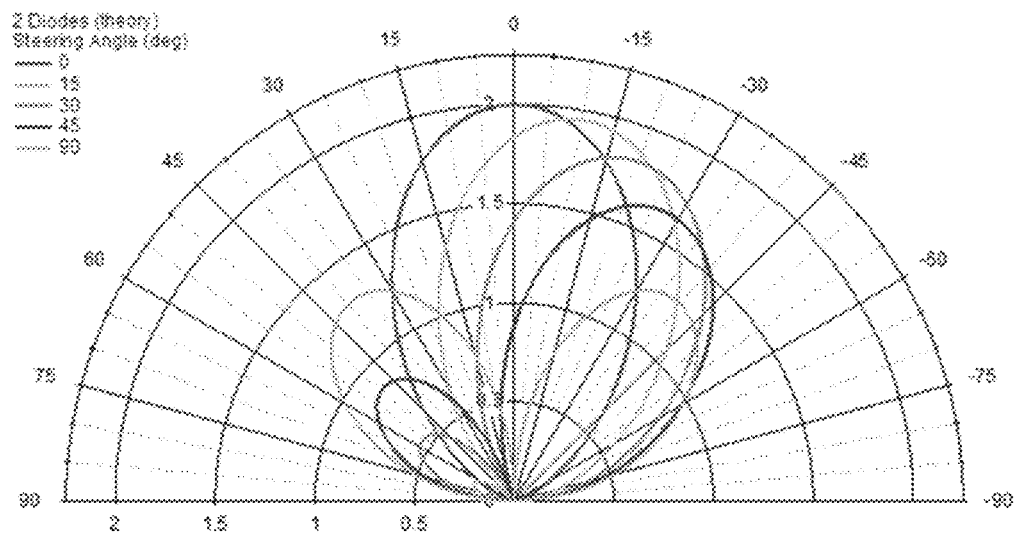
FIG. 15 is graph showing modeled acoustic beam radiation patterns.
Figure 16:
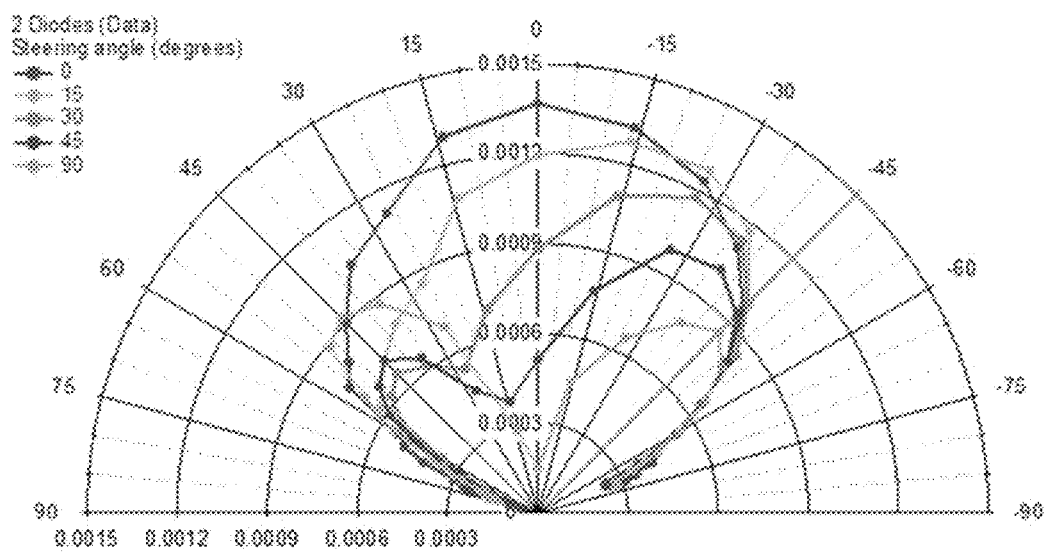
FIG. 16 is a graph showing measured beam radiation patterns corresponding to the modeled acoustic beam radiation patterns of FIG. 15.

Additionally, or alternatively, as shown in FIG. 12, two laser diode 54 elements may be used to transmit optically modulated carriers at continuous wave frequencies. The optical carrier 58, such as a piezotronics contact ultrasonic transducer, may generate the photo-acoustic response and elastic wave propagation into the biological tissue 56. The two laser diodes 54 may cause an interference pattern that can produce a steerable elastic wave, as shown in FIGS. 13 and 14. For example, as shown in FIGS. 13 and 14, a 50 kHz elastic wave frequency may be generated at the tissue sample surface due to absorption of an optical pulse at a pulse repetition frequency of about 50 kHz. As a result, the beam radiation power is generated, as shown in FIGS. 15 and 16, in response to excitation of two adjacent laser diodes 54. More specifically, FIG. 15 shows the modeled/predicted beam pattern, while FIG. 16 shows the measured pattern using a Piezotronics contact ultrasonic transducer, for example.

Figure 17:
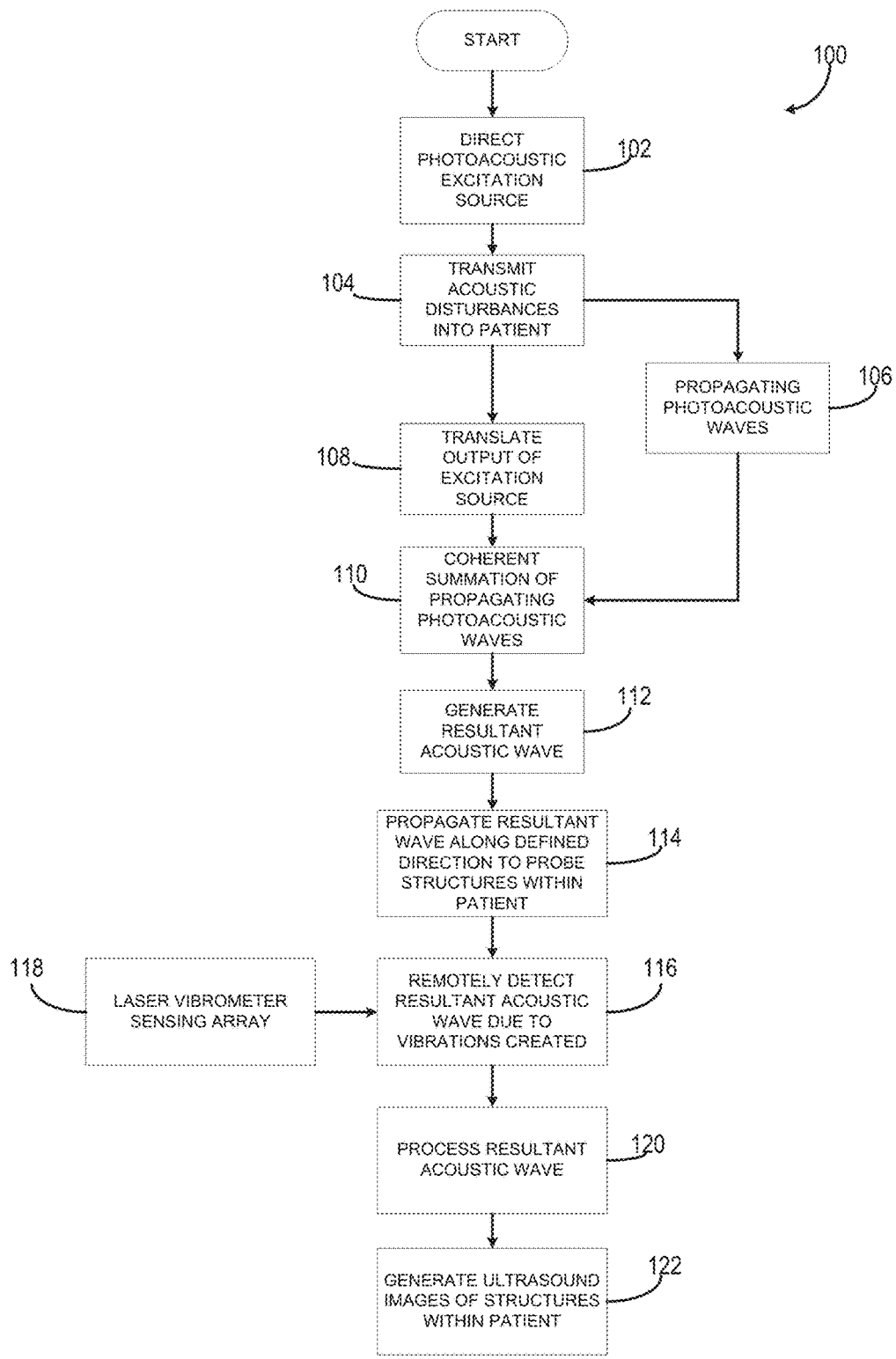
FIG. 17 is a flow chart setting forth the steps of processes for generating ultrasound images in accordance with the present invention.

Referring now to FIG. 17, a flow chart setting forth exemplary steps 100 for generating ultrasound images of structures within the patient is provided. To start the process, a photoacoustic excitation source, such as the laser source 12 shown in FIG. 3A or 3B, is directed into a scanning mirror at process block 102. The source of acoustic energy (i.e., the photoacoustic excitation source) may be, in contrast to the omni-directional acoustic energy used in conventional ultrasound imagers, a source that provides additional positional information not available via conventional ultrasound techniques. Specifically, the photoacoustic excitation source may determine not only the range to the scattering object but also its direction. It also offers the advantage over current photoacoustic techniques of a greatly enhanced signal strength.

As the laser source, for example the CW laser source, is directed into the scanning mirror, the beam is directed towards the patient, thereby transmitting acoustic disturbances into the patient at process block 104. The acoustic disturbances result in propagating photoacoustic waves across the patient at process block 106. At process block 108, output generated by the photoacoustic excitation source is translated along the patient, for example, at the speed of sound, in a defined direction to cause a coherent summation of the propagating photoacoustic waves at process block 110. The coherent summation of the propagating photoacoustic waves at process block 110 results in generation of a directional resultant wave at process block 112.

Figure 20:
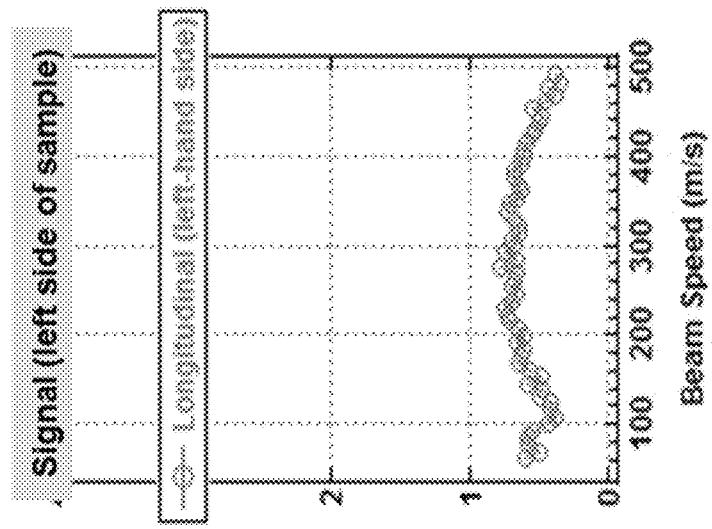
FIG. 20 is a graph showing a continuous wave laser swept at various beam speeds at a left side of a sample.
Figure 18:
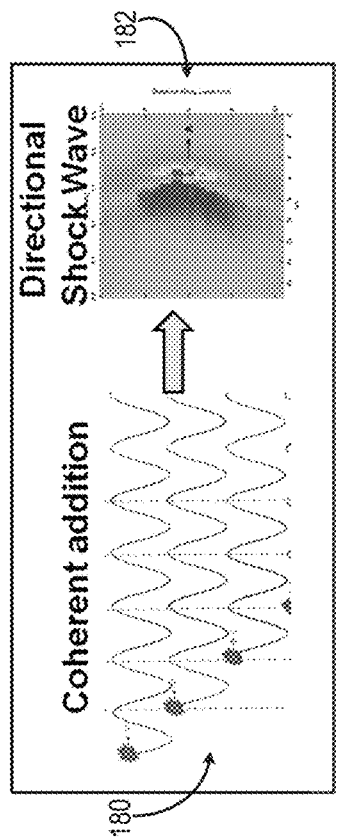
FIG. 18 is a diagram showing coherent addition of photoacoustic waves resulting in directional acoustic waves with a relatively strong signal amplitude.
Figure 19:
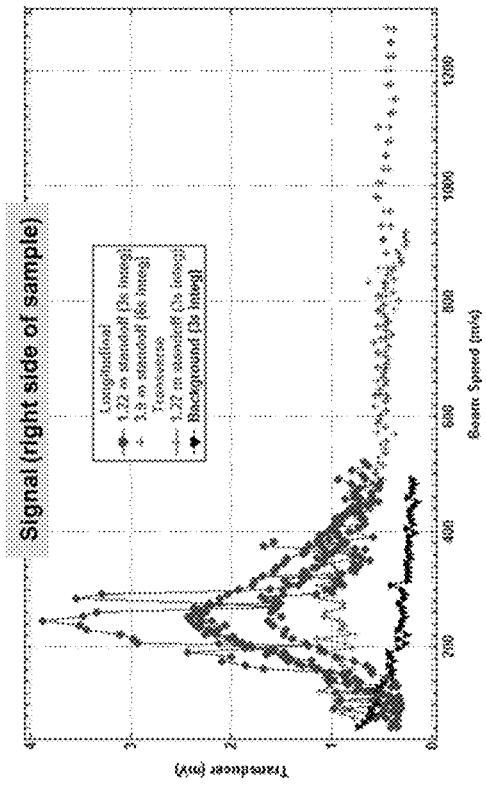
FIG. 19 is a graph showing a continuous wave laser swept at various beam speeds at a right side of a sample.
Figure 21:
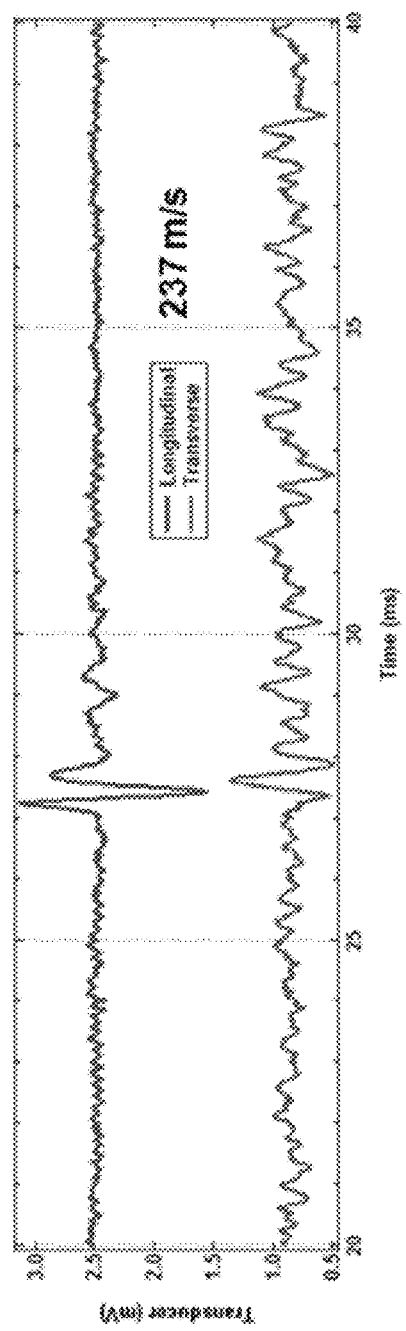
FIG. 21 is a graph showing photoacoustic signals maximized at a predetermined beam sweep speed across the skin surface sample.
Figure 22:
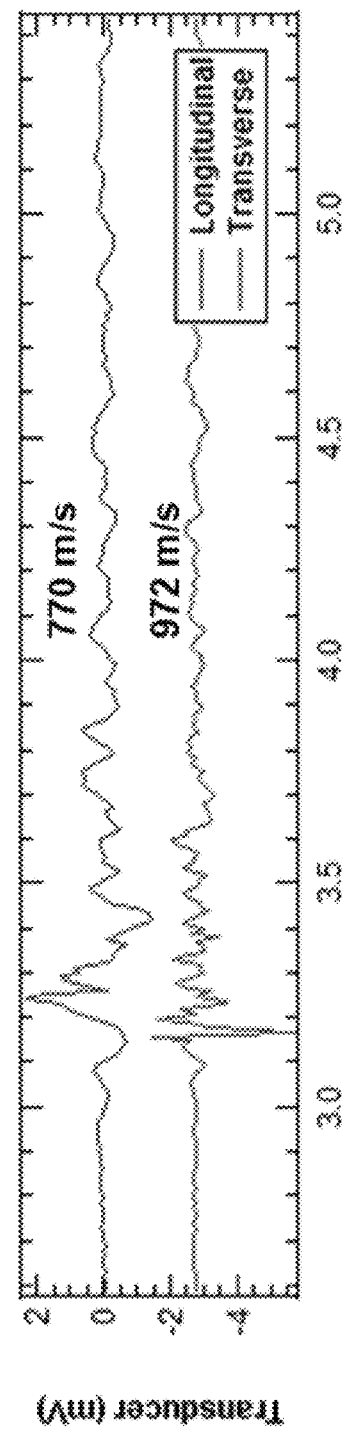
FIG. 22 is a graph showing photoacoustic signals generated at a predetermined beam sweep speeds through a bone sample.

As one example, as shown in FIG. 18, coherent summation of the propagating photoacoustic waves 180 has the advantage that the wave amplitudes, rather than intensities, add, leading to a stronger overall resultant wave 182. In addition, the scattered acoustic energy may yield information about subsurface structures. As shown in the graphs of FIGS. 19 and 20, for example, the CW laser swept at various speeds from the left side of the sample to the right side of the sample successfully induces acoustic signals. As shown in FIG. 21, the photoacoustic signal is maximized at a beam sweep speed of about 237 meters/second for a skin sample. Similarly, as shown in FIG. 22, the CW laser swept at various speeds across bone, for example, also successfully induces acoustic signals. The photoacoustic signal in this example, is maximized at about 770 meters/second in the longitudinal direction, and about 872 meters per second in the transverse direction.

Returning to FIG. 17, the resultant wave may propagate along the defined direction to probe structures of the patient's body at process block 114. At process block 116, vibrations may be detected at a surface of the patient that are created by the backscatter of the resultant wave as a result of probing structures within the patient at process block 114. The vibrations may be detected using a laser vibrometer sensing array, for example, provided at block 118. The resultant wave generated at process block 112 may then be processed at process block 120. Ultrasound images of structures within the patient may then be generated at process block 122 using the vibrations detected at the surface of the patient at process block 116.

The above-described method may be used, for example, in real-time surgical imaging guidance, detection of traumatic brain injury, internal bleeding detection and imaging, bone health monitoring, organ and tissue imaging, dynamic vital sign monitoring such as breathing rates and pulse rates from standoff. Additionally, the above-described method may be used in diagnosing vascular issues (e.g., pre-varicose veins), dermal anomalies, dehydration, BMI, or hidden sub-dermal implants.

The optical image acquisition approach described herein may have a number of advantages over contact transducer measurements. First, spatial sampling can approach sub-millimeter resolution using coherent multipixel arrays. In addition, measurements can access injured body regions, surfaces, skin conditions, open wounds or regions during surgery, difficult and awkward to reach regions, while no physical pressure of the device is applied to the skin or body. Injury to operators may be reduced due to device pressure applications to patients, and there is no need or contamination from coupling gels (as in the case of contact ultrasound devices). Lastly, the optical image acquisition approach exhibits limited SNR variability due to applied hand pressure as in the case of contact transducers.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating ultrasound images of a patient, the method comprising the steps of:
   a) directing a photoacoustic excitation source into a scanning mirror that is configured to transmit acoustic energy into the patient, and translate the acoustic energy in a defined direction at a speed of sound, wherein the acoustic energy induces propagating photoacoustic waves in the patient;
   b) translating the acoustic energy along the patient at the speed of sound using the scanning mirror to cause a coherent summation of the propagating photoacoustic waves and, thereby, at least one resultant wave that propagates along the defined direction to probe structures within the patient;
   c) detecting vibrations at a surface of the patient created by a backscatter of the least one resultant wave from the structures within the patient; and
   d) generating ultrasound images of the structures within the patient using the vibrations detected at the surface of the patient in step c).

2. The method as recited in claim 1, wherein the photoacoustic excitation source includes a laser.

3. The method as recited in claim 2, wherein the laser has one of a continuous wave output and an output with a modulating frequency between about 0 Hz to about 10 MHz.

4. The method as recited in claim 2, wherein the laser produces a laser beam and the scanning mirror is configured to move the laser beam along the defined direction.

5. The method as recited in claim 1, wherein the photoacoustic excitation source includes at least one of a directed source of radio frequency energy and microwave energy.

6. The method as recited in claim 1, wherein detecting vibrations at the surface of the patient created by backscatter of the least one resultant wave is performed using at least one of a laser vibrometer sensing array and an ultrasonic transducer receiver.

7. The method as recited in claim 6, wherein the laser vibrometer sensing array emits a beam of light configured to be delivered to at least one of an eye and skin of the patient.

8. The method as recited in claim 6, wherein the laser vibrometer sensing array is configured to perform Doppler tracking to compensate for movement of the patient.

9. The method as recited in claim 6, wherein the laser vibrometer sensing array is configured to measure the vibrations at the surface of the patient over a frequency band of about 1 Hz to about 40 MHz.

10. The method as recited in claim 6, wherein the laser vibrometer sensing array is at least one of a coherent multipixel imaging system and a digital focal plane array.

11. The method as recited in claim 1, wherein the photoacoustic excitation source includes a handheld device arranged remotely from the patient.

12. The method as recited in claim 1, wherein the ultrasound images include three-dimensional (3D) images and the structures within the patient includes at least one of a brain and a bone.

13. The method as recited in claim 1, wherein at least one of the photoacoustic excitation source and the scanning mirror are configured to translate the acoustic energy at the speed of sound.

14. A system for generating ultrasound images of a patient, the system comprising:
   a photoacoustic excitation source configured to direct light into a scanning mirror to produce acoustic energy into the patient inducing propagating photoacoustic waves, wherein the scanning mirror is configured to translate the acoustic energy in a defined direction at a speed of sound;
   a sensor configured to detect vibrations at a surface of the patient created by the propagating photoacoustic waves;
   a data acquisition system configured to acquire signals corresponding to vibrations detected by the sensor;
   a processor having access to the data acquisition system and configured to carry out the steps of:

i) directing at least the scanning mirror to translate the acoustic energy along the patient at the speed of sound to cause a coherent summation of the propagating photoacoustic waves and, thereby, generate at least one resultant wave that propagates along the defined direction to probe structures within the patient;

ii) controlling the data acquisition system to acquire signals corresponding to vibrations at the surface of the patient created by a backscatter of the at least one resultant wave from the structures within the patient; and iii) generating ultrasound images of the structures within the patient using the signals acquired.

15. The system as recited in claim 14, wherein the photoacoustic excitation source includes a laser.

16. The system as recited in claim 15, wherein the laser has one of a continuous wave output and an output with a modulating frequency between about 0 kHz to about 10 MHz.

17. The system as recited in claim 16, wherein the laser produces a laser beam and the scanning mirror is configured to move the laser beam along the defined direction.

18. The system as recited in claim 14, wherein the photoacoustic excitation source includes at least one of a directed source of radio frequency energy and microwave energy.

19. The system as recited in claim 14, wherein the sensor includes at least one of a laser vibrometer sensing array and an ultrasonic transducer receiver.

20. The system as recited in claim 19, wherein the laser vibrometer sensing array emits a beam of light configured to be delivered to at least one of an eye and skin of the patient.

21. The system as recited in claim 19, wherein the laser vibrometer sensing array is configured to perform Doppler tracking to compensate for movement of the patient.

22. The system as recited in claim 19, wherein the laser vibrometer sensing array is configured to measure the vibrations at the surface of the patient over a frequency band of about 1 Hz to about 40 MHz.

23. The system as recited in claim 19, wherein the laser vibrometer sensing array is at least one of a coherent multipixel imaging system and a digital focal plane array.

24. The system as recited in claim 14, wherein the photoacoustic excitation source includes a handheld device arranged remotely from the patient.

25. The system as recited in claim 14, wherein the ultrasound images include three-dimensional (3D) images and the structures within the patient includes at least one of a brain and a bone.

26. The system as recited in claim 14, wherein at least one of the photoacoustic excitation source and the scanning mirror are configured to translate the acoustic energy at the speed of sound.

27. A method for generating ultrasound images of a patient, the method comprising the steps of:

a) directing a laser beam, produced by a laser source, toward the patient to induce propagating photoacoustic waves therein;

b) translating the laser beam along the patient at a speed of sound using a scanning mirror to cause a coherent summation of the propagating photoacoustic waves and, thereby, at least one resultant wave that propagates along the defined direction to probe structures within the patient, wherein the scanning mirror is configured to translate the laser beam produced by the laser source in a defined direction at the speed of sound;

c) detecting vibrations, using a laser vibrometer sensing array, at a surface of the patient created by a backscatter of the least one resultant wave from the structures within the patient; and d) generating ultrasound images of the structures within the patient using the vibrations detected at the surface of the patient in step c).

28. The method as recited in claim 27, wherein the laser has one of a continuous wave output and an output with a modulating frequency between about 0 kHz to ab out 10 MHz.

29. The method as recited in claim 27, wherein the laser beam is directed into a scanning mirror configured to move the laser beam along the defined direction.

30. The method as recited in claim 29, wherein at least one of the laser source and the scanning mirror are configured to translate the laser beam at the speed of sound.

31. The method as recited in claim 27, wherein the laser vibrometer sensing array includes an ultrasonic transducer receiver.

32. The method as recited in claim 27, wherein the laser vibrometer sensing array emits a beam of light configured to be delivered to at least one of an eye and skin of the patient.

33. The method as recited in claim 27, wherein the laser vibrometer sensing array is configured to perform Doppler tracking to compensate for movement of the patient.

34. The method as recited in claim 27, wherein the laser vibrometer sensing array is configured to measure the vibrations at the surface of the patient over a frequency band of about 1 Hz to about 40 MHz.

35. The method as recited in claim 27, wherein the laser vibrometer sensing array is at least one of a coherent multipixel imaging system and a digital focal plane array.

36. The method as recited in claim 27, wherein the laser source includes a handheld device arranged remotely from the patient.

37. The method as recited in claim 27, wherein the ultrasound images include three-dimensional (3D) images and the structures within the patient includes at least one of a brain and a bone.

38. The method as recited in claim 27, wherein directing the laser source toward the patient is performed to transmit a acoustic energy into the patient.

39. A system for generating ultrasound images of a patient, the system comprising:

a laser source configured to produce a laser beam configured to induce propagating photoacoustic waves in a patient;

a laser vibrometer sensing array configured to detect vibrations at a surface of the patient created by the propagating photoacoustic waves;

a scanning mirror configured to scan the laser beam produced by the laser source in a defined direction at a speed of sound;

a data acquisition system configured to acquire signals corresponding to vibrations detected by the laser vibrometer sensing array;

a processor having access to the data acquisition system and configured to carry out the steps of:

i) controlling the scanning mirror to translate the laser beam along the patient at the speed of sound to cause a coherent summation of the propagating photoacoustic waves and, thereby, generate at least one resultant wave that propagates along the defined direction to probe structures within the patient;

ii) controlling the data acquisition system to acquire the signals corresponding to vibrations at the surface of the patient created by a backscatter of the at least one resultant wave from the structures within the patient; and iii) generating ultrasound images of the structures within the patient using the signals acquired.

40. The system as recited in claim 39, wherein the laser has one of a continuous wave output and an output with a modulating frequency between about 0 kHz to about 10 MHz.

41. The system as recited in claim 39, wherein the laser beam is directed into a scanning mirror configured to move the laser beam along the defined direction.

42. The system as recited in claim 41, wherein at least one of the laser source and the scanning mirror are configured to translate the laser beam at the speed of sound.

43. The system as recited in claim 39, wherein the laser vibrometer sensing array includes an ultrasonic transducer receiver.

44. The system as recited in claim 39, wherein the laser vibrometer sensing array emits a beam of light configured to be delivered to at least one of an eye and skin of the patient.

45. The system as recited in claim 39, wherein the laser vibrometer sensing array is configured to perform Doppler tracking to compensate for movement of the patient.

46. The system as recited in claim 39, wherein the laser vibrometer sensing array is configured to measure the vibrations at the surface of the patient over a frequency band of about 1 Hz to about 40 MHz.

47. The system as recited in claim 39, wherein the laser vibrometer sensing array is at least one of a coherent multipixel imaging system and a digital focal plane array.

48. The system as recited in claim 39, wherein the laser source includes a handheld device arranged remotely from the patient.

49. The system as recited in claim 39, wherein the ultrasound images include three-dimensional (3D) images and the structures within the patient includes at least one of a brain and a bone.

50. The system as recited in claim 39, wherein the laser source is directed towards the patient to transmit a acoustic energy into the patient.

* * * * *

UNITED STATES PATENT AND TRADEMARK OFFICE
CERTIFICATE OF CORRECTION

PATENT NO. : 10,456,044 B2
APPLICATION NO. : 14/538698
DATED : October 29, 2019
INVENTOR(S) : Robert W. Haupt et al.

It is certified that error appears in the above-identified patent and that said Letters Patent is hereby corrected as shown below:

In the Claims

Column 18, Claim 28, Line 10, "ab out" should be --about--.

Signed and Sealed this
Twenty-fourth Day of December, 2019

Andrei Iancu
*Director of the United States Patent and Trademark Office*